(12) United States Patent
Lysyansky et al.

(10) Patent No.: US 7,857,765 B2
(45) Date of Patent: Dec. 28, 2010

(54) PROTOCOL-DRIVEN ULTRASOUND EXAMINATION

(75) Inventors: Peter Lysyansky, Haifa (IL); Israel Raz, Highland Park, IL (US); Zvi Friedman, Kiryat Byalik (IL)

(73) Assignee: General Electric Company, Schenectady, NY (US)

( * ) Notice: Subject to any disclaimer, the term of this patent is extended or adjusted under 35 U.S.C. 154(b) by 747 days.

(21) Appl. No.: 11/697,111

(22) Filed: Apr. 5, 2007

(65) Prior Publication Data

US 2007/0173721 A1 Jul. 26, 2007

Related U.S. Application Data

(63) Continuation of application No. 10/832,561, filed on Apr. 27, 2004, now abandoned.

(60) Provisional application No. 60/540,812, filed on Jan. 30, 2004.

(51) Int. Cl.
*A61B 8/00* (2006.01)

(52) U.S. Cl. .................. 600/437; 600/439; 600/443; 600/447; 600/450; 600/453; 600/461; 600/481; 705/3; 700/17

(58) Field of Classification Search ............... 600/407, 600/437, 439, 443, 447, 454, 461, 463; 705/3; 700/17
See application file for complete search history.

(56) References Cited

U.S. PATENT DOCUMENTS 5,797,849 A * 8/1998 Vesely et al. ............ 600/461

5,986,662 A 11/1999 Argiro et al.
6,019,725 A * 2/2000 Vesely et al. ............ 600/447

(Continued)

FOREIGN PATENT DOCUMENTS

EP 1 454 585 A1 9/2001

(Continued)

OTHER PUBLICATIONS

Website information: Philips introduces new ultrasound technologies and products that enhance the clinical value of volumetric imaging, provide new tools for interventional procedures, shorten exam times and facilitate pediatric echo:, Oct. 12, 2006, http://www.medical.philips.com/au/news/content/file_1302.html (last visited Apr. 4, 2007).

(Continued)

*Primary Examiner*—Brian Casler
*Assistant Examiner*—Baisakhi Roy
(74) *Attorney, Agent, or Firm*—McAndrews, Held & Malloy, Ltd.; Michael A. Dellapenna (57) ABSTRACT

The present invention relates to a system and method for performing a protocol-driven ultrasound examination for generating an image of moving cardiac structure and blood of a heart. One embodiment comprises a front-end and at least one processor. The front end is arranged to transmit ultrasound waves into the moving cardiac structure and blood, generating received signals in response to the ultrasound waves backscattered from the moving cardiac structure and blood. The at least one processor, responsive to the received signals, acquires at least one image of the structure in at least one of a predetermined order and a predefined protocol, and selects at least one of the acquired images taken along at least one of a given view and study.

18 Claims, 4 Drawing Sheets

U.S. PATENT DOCUMENTS

| | | | |
|---|---|---|---|
| 6,063,030 A | 5/2000 | Vara et al. | |
| 6,086,540 A | 7/2000 | Bonneville et al. | |
| 6,174,285 B1 | 1/2001 | Clark | |
| 6,217,515 B1* | 4/2001 | Yamakawa et al. | 600/437 |
| 6,246,898 B1* | 6/2001 | Vesely et al. | 600/424 |
| 6,458,081 B1 | 10/2002 | Matsui et al. | |
| 6,468,212 B1 | 10/2002 | Scott et al. | |
| 6,488,629 B1 | 12/2002 | Saetre et al. | |
| 6,540,676 B2 | 4/2003 | Kamiyama | |
| 6,599,244 B1 | 7/2003 | Epps et al. | |
| 6,674,879 B1 | 1/2004 | Weisman et al. | |
| 6,773,398 B2 | 8/2004 | Ogasawara et al. | |
| 6,827,684 B2 | 12/2004 | Maruyama | |
| 6,904,161 B1 | 6/2005 | Becker et al. | |
| 6,951,543 B2 | 10/2005 | Roundhill | |
| 6,953,433 B2 | 10/2005 | Kerby et al. | |
| 6,979,294 B1 | 12/2005 | Selzer et al. | |
| 7,022,075 B2 | 4/2006 | Grunwald et al. | |
| 7,092,749 B2* | 8/2006 | Fowkes et al. | 600/407 |
| 2004/0066389 A1 | 4/2004 | Skyba et al. | |
| 2004/0077952 A1* | 4/2004 | Rafter et al. | 600/481 |
| 2004/0254465 A1* | 12/2004 | Sano et al. | 600/443 |
| 2004/0267122 A1 | 12/2004 | Nadadur et al. | |
| 2005/0049506 A1 | 3/2005 | Jackson et al. | |
| 2005/0096539 A1* | 5/2005 | Leibig et al. | 600/437 |
| 2006/0170714 A1 | 8/2006 | Kanda | |

FOREIGN PATENT DOCUMENTS

| | | |
|---|---|---|
| WO | WO 03/043501 A1 | 5/2003 |

OTHER PUBLICATIONS

Website information: Philips, "Redesigning workflow and throughput," http://www.medical.philips.com/us/products/ultrsound/general/iu22/workflow.html (last visited Apr. 4, 2007).

Website information: "Toshiba Aplio Ultrasound Demonstrates New Technique to Enhance Diagnosis and Treatment of Heart Failure," Mar. 2, 2005, http://saslesandmarketingnetwork.com/news_release.php?ID=2003584 (last visited Apr. 4, 2007).

* cited by examiner

PROTOCOL-DRIVEN ULTRASOUND EXAMINATION

RELATED APPLICATIONS/INCORPORATION BY REFERENCE

This application is a continuation of U.S. patent application Ser. No. 10/832,561, filed on Apr. 27, 2004, which claims the benefit of U.S. Provisional Patent Application No. 60/540,812, filed on Jan. 30, 2004, both of which are incorporated by reference in their entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present invention relate to a system and method for performing an ultrasound examination. More specifically, embodiments of the present invention relate to a system and method for performing a protocol-driven ultrasound examination to image a structure, moving cardiac structure and blood of a heart for example.

It should be appreciated that ultrasonic examinations are generally an operator-dependent complicated task performed by highly skilled operators. Moreover, due mainly to budgetary constraints, the examination (i.e., acquisition of one or more images) is often performed by a technologist, whereas the review and clinical interpretation of the acquired data (i.e., reading the one or more acquired images) is performed by a physician. This is generally true for a variety of applications such as general radiology, vascular ultrasonic examination, echocardiography, and during cardiac surgery, where the anesthesiologist performs the ultrasonic examination.

In order to assure the quality of this complex diagnostic process, several professional societies (e.g., the American Society for Echo, the Society for Cardiovascular Anesthesiology, etc.) have published recommended guidelines for this process. The guidelines advocate following a prescribed protocol that includes acquiring a sequence of several different views (up to 20 views for example) necessary to complete a comprehensive examination. These views may be obtained by positioning the probe at different locations, viewing angles, and orientations.

Cardiac Ultrasound imaging, using a Trans Esophageal (TEE) probe for example, is an important tool in assessing and monitoring heart function during cardiac and other surgical procedures. Such imaging provides real-time information, which the surgeon depends on in planning, monitoring, and assessing surgical success in the operating room (OR). It should be appreciated that the embodiments of the present invention are not limited to performing cardiac ultrasound imaging using a TEE probe, but other fields of diagnostic examinations (including ultrasonic examinations on non-cardiac structure) are contemplated, some of which are discussed previously.

Hospitals differ in terms of the protocols (i.e., the number and orders of views) they follow for TEE monitoring in different procedures (e.g., cardiac bypass, valve repair, etc.). Anesthesiology fellows and other professionals (or users) seeking to develop these skills are trained to follow the strict protocols adopted by each hospital. The only such tool to guide them during surgery, while they develop expertise in this area comprises handouts, drawings, "cheat sheets," etc. This method is cumbersome and prone to error.

Situations frequently occur in the OR wherein a clip taken at a given view (e.g., 4-chamber view) must be compared to a clip taken previously at the same given view. This is a laborious task, since the archive of clips or images from this surgery may already contain a large number of clips of different views. Therefore the search and selection of the appropriate clips may be tedious and labor intensive. It should be appreciated that these situations referred to above generally occur as a result of an emergency in the operation procedure, placing the user under stress.

Further limitations and disadvantages of conventional and traditional approaches will become apparent to one of skill in the art, through comparison of such systems with the present invention as set forth in the remainder of the present application with reference to the drawings.

BRIEF SUMMARY OF THE INVENTION

Embodiments of the present invention relate to an ultrasound system and method for performing an ultrasound examination. More specifically, embodiments of the present invention relate to a system and method for performing a protocol-drive ultrasound examination to image a structure, moving cardiac structure and blood of a heart for example.

One or more embodiments of the system and method of the present invention provides anesthesiologists, monitoring professionals and other users with an efficient tool used in training, simulation, and surgical planning. Embodiments of the present invention may improve consistency in operation, quality control, and workflow. Embodiments may improve the quality of the examination, speed of operation, and standard of care, in addition to facilitating communication and exchanging expert knowledge among professionals worldwide.

An apparatus is provided for performing a protocol-driven ultrasound examination for generating an image of moving cardiac structure and blood of a heart for example. This embodiment comprises a front-end and at least one processor. The front end is arranged to transmit ultrasound waves into the moving cardiac structure and blood, generating received signals in response to the ultrasound waves backscattered from the moving cardiac structure and blood. The at least one processor, responsive to the received signals, acquires at least one image of the structure in at least one of a predetermined order and a predefined protocol, and selects at least one of the acquired images taken along at least one of a given view and study.

Embodiments of the apparatus may include a display processor and monitor for displaying the at least one acquired image. Other embodiments comprise the at least one processor adapted to label the at least one acquired image.

One embodiment of the present invention relates to a method for performing an examination on a structure using an ultrasound system. This embodiment of the method comprises acquiring at least one image of the structure in at least one of a predetermined order and a predefined protocol. The method further comprises selecting at least one of the acquired images taken along at least one of a given view and study.

Embodiments are contemplated in which the at least one acquired image is displayed on an ultrasound system display, where the at least one acquired image may be displayed simultaneously with at least one stored image or at least one icon associated with the acquired image.

Embodiments of the invention are further contemplated in which the at least one predefined protocol is user configurable, wherein the configurable predefined protocol comprises at least one view. At least one selected image may be selected and/or stored wherein at least one stored image may be retrieved using a label. Further, at least two or more icons may be arranged in a predetermined scanning order.

Still another embodiment of the present invention relates to a method for performing an examination on moving cardiac structure and blood in a heart. This embodiment comprises selecting at least one of a predetermined order and predefined protocol for acquiring at least one image of the moving cardiac structure and blood in the heart. The least one image is acquired in at least one of a predetermined order and a predefined protocol, forming at least one clip. The at least one clip is selected, labeled and stored.

One or more embodiments of the method comprise displaying at least one acquired image on a display, wherein the at least one acquired image may be display simultaneously with the at least one clip and/or at least one icon associated with the acquired image.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION OF THE INVENTION

Embodiments of the present invention relate to an ultrasound system and method for performing an ultrasound examination. More specifically, embodiments of the present invention relate to an system and method for performing an examination of a structure, a protocol-drive ultrasound examination to image a heart for example. Moving cardiac structure and blood may be monitored to accomplish this function. As used herein, the term structure comprises non-liquid and non-gas matter, such as cardiac tissue for example.

In at least one embodiment of the present invention, the system and method enables the user to reconstruct a scanning session following the procedure or surgery. The user may quickly access selected phases in the procedure or surgery, access specific views/studies within each phase, etc. These conventions may also be transferred to a report generation package.

TEE monitoring is currently conducted based on protocols suggested in the guidelines of various professional societies. Many professionals, especially those less experienced professionals performing ultrasound examinations, rely on external reference materials used in tandem with the ultrasound system during monitoring. One embodiment of the present invention incorporates expert knowledge regarding the protocols the user intends to follow directly into the ultrasound system, machine or method. In this manner, the user focuses on the task at hand and is not distracted during this time-critical surgical procedure.

Another embodiment relates to the efficiency of work in the OR by enabling quick comparison of the current patient situation with previous situations. Finally, embodiments of this invention may facilitate the post-surgical record review process enabling the reviewers to sort quickly through the different surgery phases and focus on selected images with minimal effort.

Figure 1:
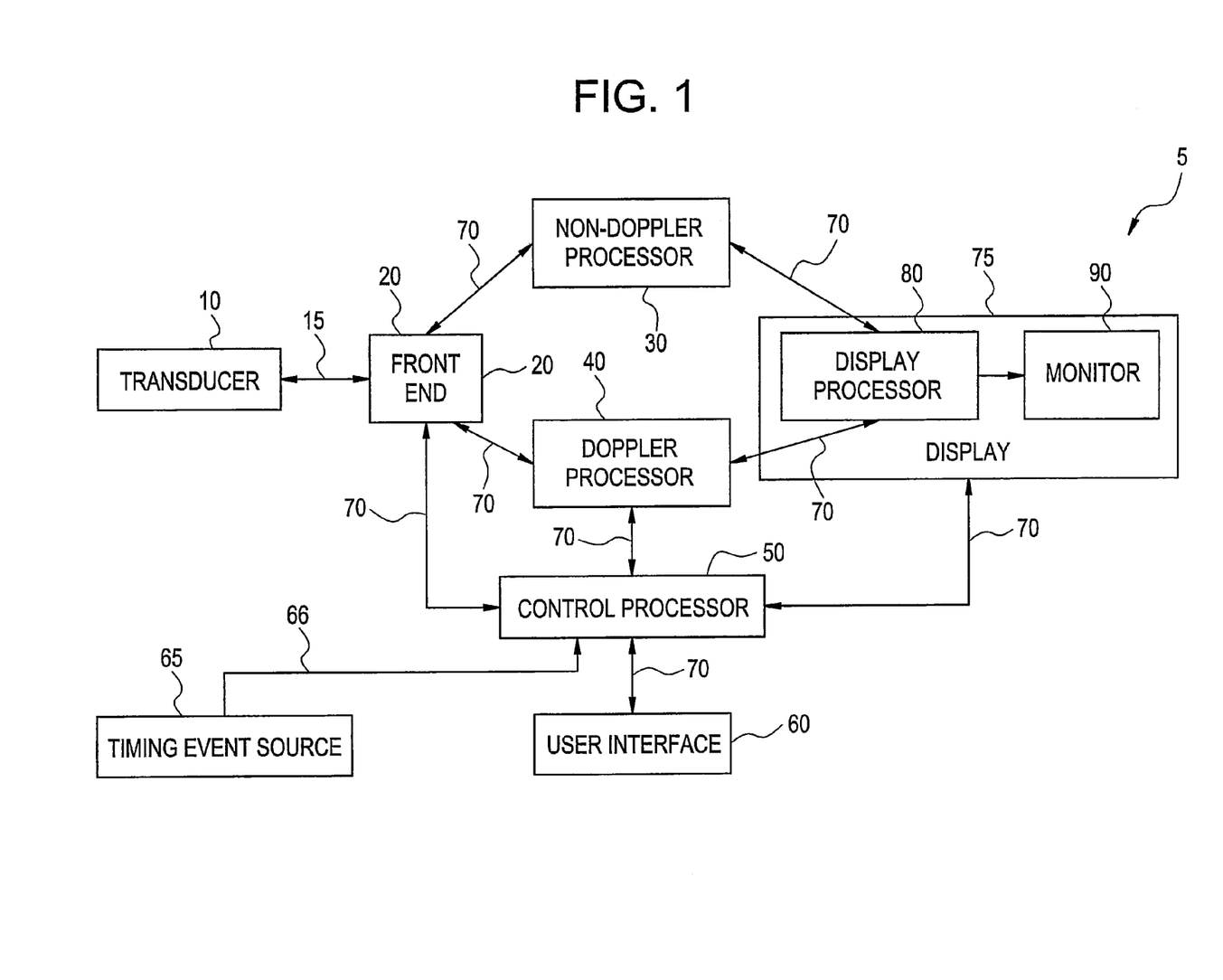
FIG. 1 depicts a block diagram of an embodiment of an ultrasound system and machine in accordance with various embodiments of the present invention.

FIG. 1 illustrates an embodiment of an ultrasound machine, generally designated 5, in accordance with embodiments of the present invention. A transducer or probe 10 (a TEE probe for example) transmits ultrasound waves into a subject by converting electrical analog signals to ultrasonic energy and receives the ultrasound waves backscattered from the subject by converting ultrasonic energy to analog electrical signals. A front-end 20, that in one embodiment comprises a receiver, transmitter, and beamformer, may be used to create the necessary transmitted waveforms, beam patterns, receiver filtering techniques, and demodulation schemes that are used for the various imaging modes. Front-end 20 performs such functions, converting digital data to analog data and vice versa. Front-end 20 interfaces to transducer or probe 10 using analog interface 15 and interfaces to a non-Doppler processor 30, a Doppler processor 40 and a control processor 50 over a bus 70 (digital bus for example). Bus 70 may comprise several digital sub-buses, each sub-bus having its own unique configuration and providing digital data interfaces to various parts of the ultrasound machine 5.

Non-Doppler processor 30 is, in one embodiment, adapted to provide amplitude detection functions and data compression functions used for imaging modes such as B-mode, M-mode, and harmonic imaging. Doppler processor 40, in one embodiment, provides clutter filtering functions and movement parameter estimation functions used for imaging modes such as tissue velocity imaging (TVI), strain rate imaging (SRI), and color M-mode. In one embodiment, the two processors, 30 and 40, accept digital signal data from the front-end 20, process the digital signal data into estimated parameter values, and pass the estimated parameter values to processor 50 and a display 75 over digital bus 70. The estimated parameter values may be created using the received signals in frequency bands centered at the fundamental, harmonics, or sub-harmonics of the transmitted signals in a manner known to those skilled in the art.

Display 75 is adapted, in one embodiment, to provide scan-conversion functions, color mapping functions, and tissue/flow arbitration functions for example, performed by a display processor 80 which accepts digital parameter values from processors 30, 40, and 50, processes, maps, and formats the digital data for display, converts the digital display data to analog display signals, and communicates the analog display signals to a monitor 90. Monitor 90 accepts the analog display signals from display processor 80 and displays the resultant image.

A user interface 60 enables user commands to be input by the operator to the ultrasound machine 5 through control processor 50. User interface 60 may comprise a keyboard, mouse, switches, knobs, buttons, track balls, foot pedals, voice control and on-screen menus, among other devices.

A timing event source 65 generates a cardiac timing event signal 66 that represents the cardiac waveform of the subject. The timing event signal 66 is input to ultrasound machine 5 through control processor 50.

In one embodiment, control processor 50 comprises the main, central processor of the ultrasound machine 5, interfacing to various other parts of the ultrasound machine 5 through digital bus 70. Control processor 50 executes the various data algorithms and functions for the various imaging and diagnostic modes. Digital data and commands may be communicated between control processor 50 and other various parts of the ultrasound machine 5. As an alternative, the functions performed by control processor 50 may be performed by multiple processors, or may be integrated into processors 30, 40, or 80, or any combination thereof. As a further alternative, the functions of processors 30, 40, 50, and 80 may be integrated into a single PC backend.

Figure 2:
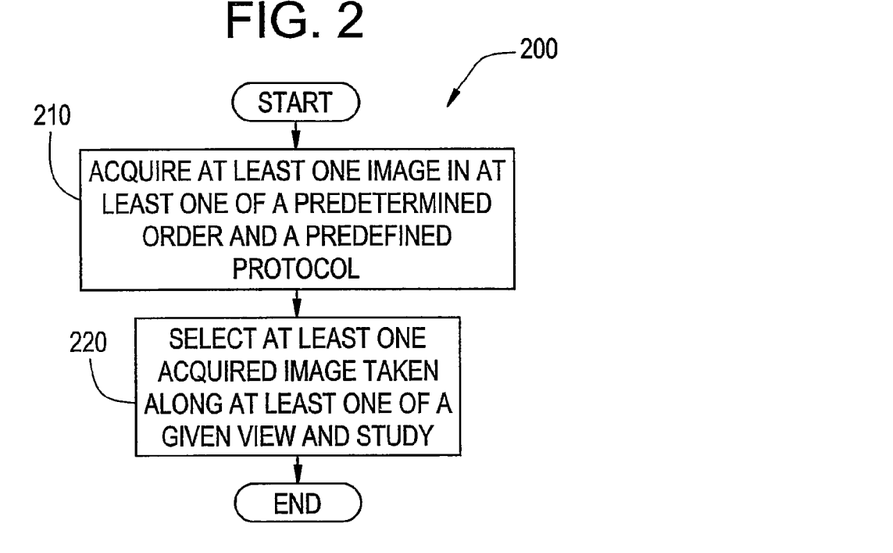
FIG. 2 depicts a high level flowchart illustrating an embodiment of a method performed by the system depicted in FIG. 1, in accordance with various embodiments of the present invention.

One embodiment of the present invention comprises a system and method for performing a protocol-driven ultrasound examination to acquire an image of a structure, moving cardiac structure and blood of a heart for example. FIG. 2 depicts a high level flow chart illustrating a method 200 for acquiring at least one image in accordance with various embodiments of the present invention. In the illustrated embodiment, method 200 comprises Step 210, which comprises acquiring at least one image in at least one of a predetermined order and a predefined protocol while imaging the heart using ultrasound system 5 for example. In one embodiment, the at least one image (or clip) is acquired automatically, and at least the protocol is configurable by the user for example. Step 220 comprises selecting at least one acquired image or clip taken at or along at least one of a given view (parasternal long axis for example) or study (MR study for example).

In at least one embodiment of the invention, application software is incorporated into an ultrasound system (running on processor 50 of ultrasound system 5 for example) enabling an examining professional or other user to program user-defined protocols into the system. Such protocols may be used to guide the examining professional through a sequence of views (e.g., 4CH, LAX, SAX, etc.) and studies (e.g., MR study, AV study, LV volume, etc.) appropriate for the procedure being performed. Thus, in at least one embodiment, the system and method provides one or more schematics of the target view/study during the examination, providing visual aids to guide the examining professional in correct positioning and orientation of the transducer or probe (a TEE probe for example) for best visualization of the targeted view. When one or more target views are acquired (forming a clip), the image may be saved with a corresponding label. The system and method proceeds to present the next view in the protocol, until the entire protocol is completed.

Figure 3:
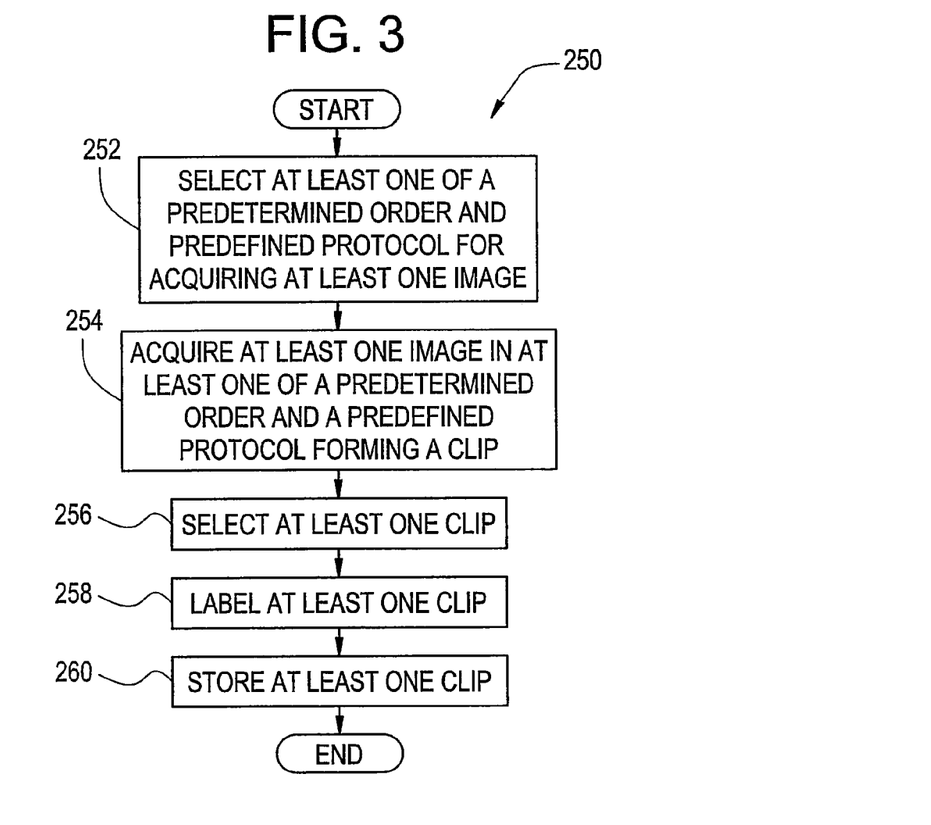
FIG. 3 depicts a detailed flowchart illustrating an embodiment of a method performed by the system depicted in FIG. 1, in accordance with various embodiments of the present invention.

FIG. 3 depicts a flow chart illustrating an embodiment of a method 250 (similar to method 200 depicted in FIG. 2) performed (using the system or machine illustrated in FIG. 1 for example) in accordance with various embodiments of the present invention. In the illustrated embodiment, method 250 comprises Step 252, which comprises selecting at least one of a predetermined order and predefined protocol for acquiring at least one image of the moving structure. In one embodiment, method 250 enables a user to select both the predetermined order and predetermined protocol.

Figure 4:
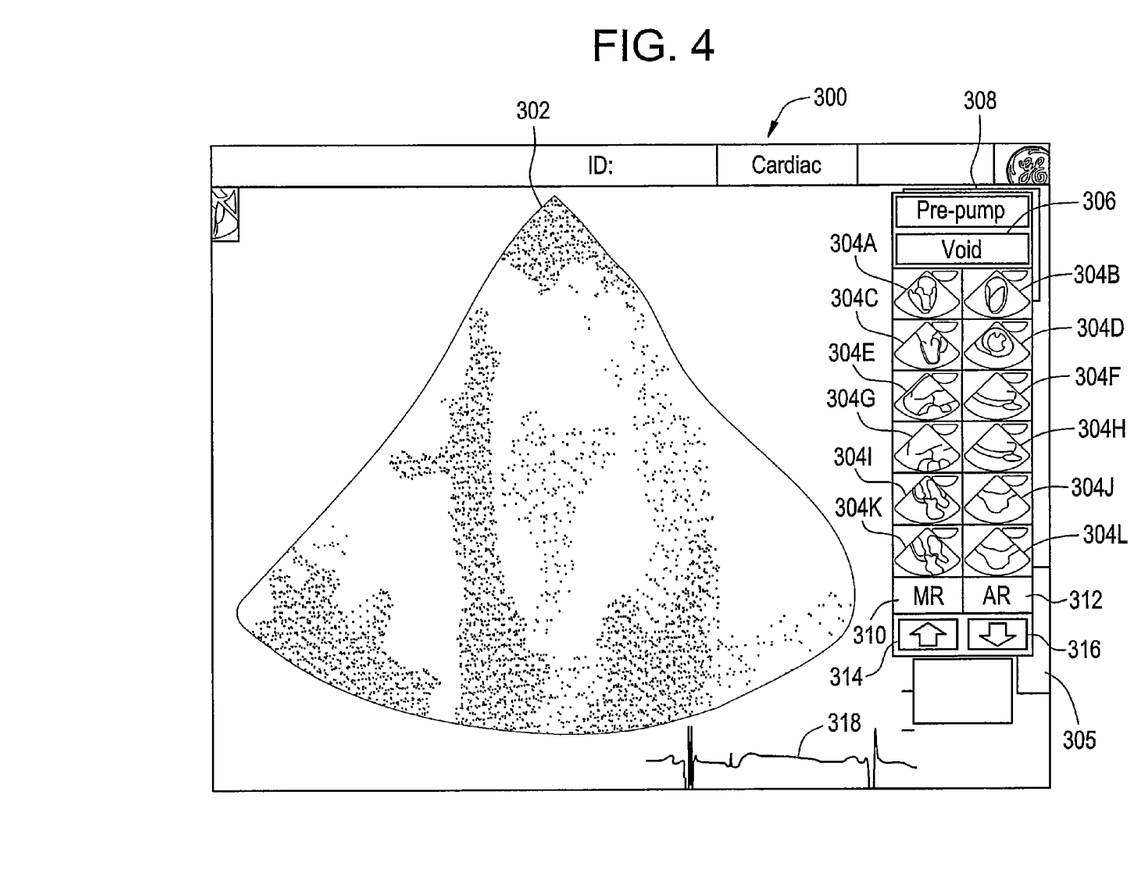
FIG. 4 depicts a view of a display displaying images and icons using the methods of FIGS. 2 and 3 in accordance with various embodiments of the present invention.

FIG. 4 illustrates a display, generally designated 300, that may be depicted or displayed on monitor 90 of the system of FIG. 1 for example. In one embodiment, display 300 includes at least one acquired image of moving cardiac structure (of a heart for example) and a series of graphical icons or labels 302A through 302L (and, in one embodiment, a void icon 306). In the illustrated embodiment, icons 302A through 302L are arranged in display 300 in a predetermined scanning order that may configured by the user. In at least one embodiment, the configurable predetermined scanning order is represented as a protocol.

Method 250 further comprises Step 254, which comprises acquiring at least one image in at least one of an predetermined order and a predefined protocol while imaging the heart using ultrasound system 5 for example. In one embodiment the predefined protocol is configurable. It is further contemplated that the at least one image or clip may be acquired automatically by the system or machine for example.

Step 256 comprises selecting at least one acquired image or clip, where the selected clip may have been taken at or along at least one of a given view (parasternal long axis for example) and study (MR study for example). In at least one embodiment, selecting the at least one clip comprises selecting at least one icon 304A-304B depicted in FIG. 4 for example. The selected icon will be highlighted in the protocol list 305 and the associated image 302 shown on display 300. In one embodiment, image 302 is shown simultaneously with the highlighted icon. Embodiments are contemplated in which the clip is selected and labeled. In at least one embodiment the clip may be selected during acquisition, selected from an archive, or some combination thereof.

In one embodiment, method 250 further comprises Step 254, which comprises labeling the at least one clip and Step 260, which comprises storing the at least one clip. It is contemplated that labeling the clip may comprise associating or more identifiers (or labels) with the clip, so that the clip may be retrieved using such identifier for example. It is contemplated that one or more clips may be stored in processor 50, another storage device on the ultrasound system (not shown in FIG. 1) or an external storage device (not shown in FIG. 1). It should be appreciated that the one or more clips may be labeled before storage or stored and then labeled.

FIG. 4 illustrates display or monitor 300, including at least one acquired image of a moving structure (moving cardiac structure of a heart for example) generally designated 302 and a protocol bar or protocol list 305. In this embodiment, the protocol bar 305 comprises the series or sequence of graphical icons or labels 302A through 302L; void icon 306; pre-pump icon 308; mitral and aortic regurgitation (alternatively referred to as "MR" and "AR" respectively) icons 310 and 312 respectively; up and down arrow icons 314 and 316 respectively. In this embodiment, icons 302A through 302L are arranged in display 300 in a predetermined scanning order that may configured by the user. It is contemplated that in one or more embodiments display 300 may provide the image 302 simultaneously with the associated icon, in addition to providing other information, including an EKG 318 for example.

In one embodiment of the present invention, the system and method may toggle between displaying and not displaying protocol list 305. When the protocol button or icon (not shown) is selected, protocol bar or list 305, including all associated icons will appear in display 300. Selecting the protocol button a second time, hides or stops displaying the protocol list 305.

As provided previously, one or more embodiments of the present invention, displays a series of graphical icons or labels 304A-304L in a configurable predetermined order of scanning (representing the protocol). The series of icons include a void icon 306. The system and method enables the user to select at least one icon. The selected icon will be in this embodiment, highlighted in the protocol list 305 and simultaneously shown on the image 302.

In this embodiment, the selected icon will be attached to the clip and will be shown on the image 302 in all operating modes (with body marks for example). The icon selection will either automatically move one step forward in the protocol list after each clip is stored or archived or not, depending on the mode of operation. The user can configure the selection between the two modes of operation.

It is further contemplated that the user may reselect an icon before or during scanning. For example, the user may reselect the icon during the clip storing process (between first and second presses or selection of the store button or icon for example). The system further enables the operator to relabel a stored or archived clip. The system enables the operator to mark an operation stage, toggling between pre-pump and post-pump status or state using the pre-pump icon 308 for example. The stored clips in a clipboard may be marked with different colored frames or borders when selected (for example the stored clips in a clipboard may have a green frame in the pre-pump status and a blue frame in the post-pump status).

In at least one embodiment, the present invention may include an automatic on-line help module providing information to guide the user in obtaining or acquiring images, wherein the information may be provided graphically, verbally or graphically and verbally. The system enables the user to configure the system to either provide or not provide this information.

It is contemplated that, in at least one embodiment, the system and method may provide for labeling one or more clips during acquisition. When a protocol button or icon (not shown) is selected, protocol list 305 may be displayed on display 300, on the right side of the display for example. In one embodiment of the invention, the system and method enables the user to toggle between pre-pump and post-pump status or state. In at least this embodiment, the pre-pump icon 308 may be used to toggle between the pre-pump and post-pump status or states. It is contemplated that at least one embodiment of the system and method starts from the pre-pump state.

Embodiments of present invention may indicate or designate which icons are selected and in what state. For example, the selected icon 304A-304L may be marked with different colored frames or borders (for example the selected icon may have a green frame in the pre-pump status and a blue frame in the post-pump frame). In one embodiment, the selected icon appears in the image 300.

It should be appreciated that the user may want to toggle between or select an image that is different from the displayed image. In at least one embodiment of the present invention, the user may change the icon either by clicking on or otherwise selecting a desired icon (if it is included in the protocol bar 305), using the arrow icons 314 and 316 or using the arrows on an associated keyboard. In at least one embodiment, the newly selected icon may also appear on the image 302.

For example, after selecting the store icon (not shown), the user may change icons. Selecting or hitting the store icon a second time enables the system to automatically jump to the next label, provided that the system was pre-configured to operate in this mode. If the void icon or Autojump Off option was selected in the protocol configuration, the system maintains the selected icon and will not jump to the next icon in the list. In one embodiment, all thumbnail images in the clipboard labeled with a currently selected label are marked with the appropriate frame.

It is contemplated that, in at least one embodiment, the system and method may provide for labeling one or more stored or archived clips. In this embodiment, the user selects the desired clip and then selects the protocol button or icon (not shown). The user selects the desired icon and selects the store button or icon.

It is contemplated that, in at least one embodiment, the system and method may provide for reviewing one or more images using a given or selected icon. To review the images using an icon, the icon in the protocol list 305 must be selected. All images associated with the selected icon will be marked or otherwise highlighted. In one embodiment, the images associated with the selected icon may be marked with a different colored frames or borders (for example the images may have a green frame in the pre-pump status and a blue frame in the post-pump status). It is contemplated that all the images associated with the selected icon may displayed simultaneously, in sequence, etc.

It should be appreciated that in at least one embodiment, the ultrasound system may operate in different modes or have different configurations. In one embodiment of the present invention, the user may configure the system to "Scan by Protocol". In this configuration, the system acquires one or more images using the icon list in the order of the icon list. Also, the system may be configured to operate in (and toggle between) "Autojump On" or "Autojump Off" modes. In the "Autojump On" mode, the system operates in protocol mode, scanning one image then jumping to the next icon in the protocol list (the next icon is marked or highlighted in the protocol list for example). In the "Autojump Off" mode, the system operates manually (i.e., the system does not jump to the next icon in the protocol list)

Other embodiments of the present invention are also contemplated. An embodiment is contemplated in which, in addition to ordering echo examination, each view/study may be linked with a set of scanning parameters, where the set of scanning parameters is optimized for this view/study. This enables the user to save time and to immediately obtain optimal image quality for all views and studies.

Other embodiments are contemplated, including the capability to link each view/study with a specific subset of parameters. This enables the user to save time by working with a short list of parameters for each view/study. These capabilities are especially important for less skilled user.

It should be appreciated that different protocols may be used depending on the procedure or surgery. Embodiments of the present invention are adapted to accommodate different protocols. More particularly, embodiments of the present invention are adapted to accommodate multiple protocols, depending on the type of procedure or surgery, enabling the user to select one protocol from among the plurality of protocols. Additionally, it is contemplated that the user may be able to define a new protocol, using one or more icons from protocols currently existing or stored on the system.

Other embodiments contemplate a link to a measurements package and automatic present and scanning mode selection.

Yet still another embodiment of the invention includes a live view module, providing for comparison of live scanning (live images for example) with previously scanned reference cine clips. In the scan-by-protocol mode of operation for example, the reference clips may always be the same view as the live image.

In one embodiment of the present invention, one or more reference clips will automatically be "zoomed" to the same scale as that of the live image. It is contemplated that in one embodiment, the system and method may accommodate at least a live image and one reference clip. In other embodiments, the system and method may accommodate a live image and two or more reference clips (alternatively referred to as "Ref1" and "Ref2"). It is contemplated that, in at least one embodiment, Ref1 and Ref2 may each comprise a family of clips with all possible labels. While scanning a live image with a given label, the corresponding clips from Ref1 and Ref2 with the corresponding labels may be displayed. In at least one embodiment, the corresponding clips of Ref1 and Ref2 are rescaled to the scale of the live image.

Figure 5:
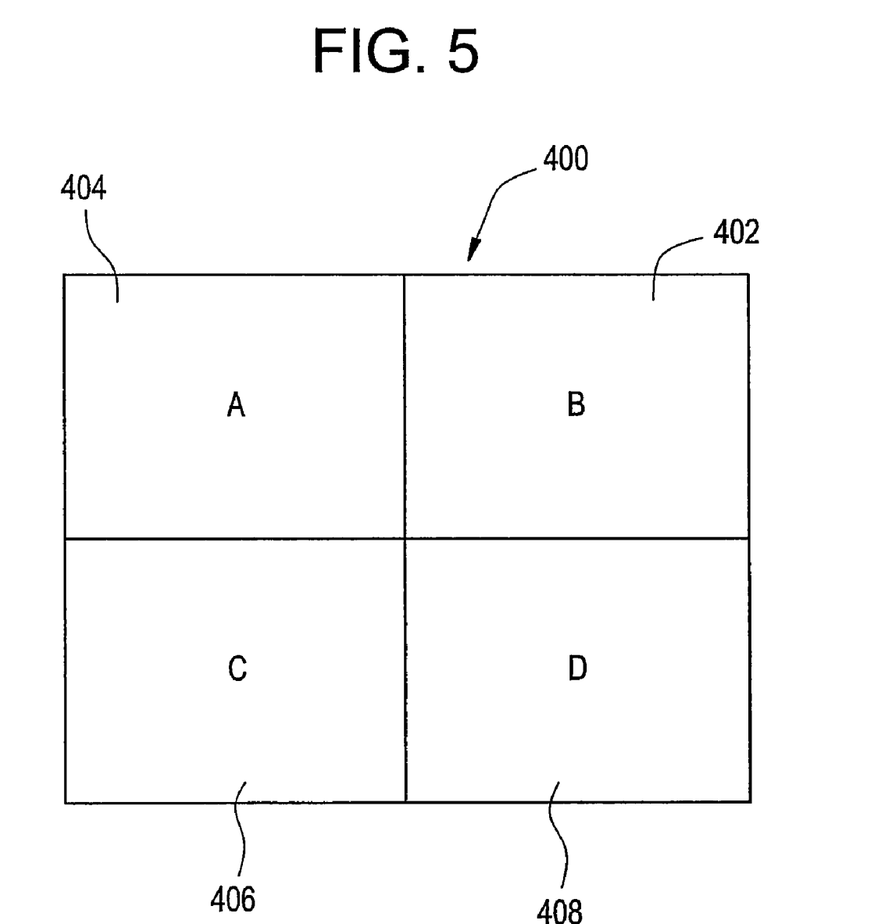
FIG. 5 depicts a schematic view of a display of the system of FIG. 1 comprising four quadrants illustrating at least one live view and reference clips in accordance with various embodiments of the present invention.

FIG. 5 depicts a schematic view of a display, generally designated 400, that may be depicted or displayed on monitor 90 of the system of FIG. 1 for example. In one embodiment, display 400 provides at least one live view and one reference clip in accordance with various embodiments of the present invention. More particularly, display 400 comprises four quadrants A, B, C and D (designated 404, 402, 406 and 408 respectively) depicting at least one live view, Ref1 and Ref2 for example.

In at least one embodiment, the user selects the live view module by selecting or toggling an LV Monitoring key or icon (not shown). The monitor depicts display 400, wherein display 90 is split into four quadrants for example. In this embodiment, a live image is displayed in quadrant B 402. Selecting, depressing or toggling an Ref1 button or icon (not shown) enables the system to capture a clip of the live image into Ref1, which may be displayed in quadrant A 404. Ref2 may be displayed in quadrant C 406. It should be appreciated that, as the live image may be scanned with a multitude of labels Ref1 (and/or Ref2) actually represents a series of clips with different labels. When a specific label is assigned to the live image, the corresponding clips of Ref1 and Ref2 are displayed in the quadrants A and C. If there is no Ref1 or Ref2 image with the present label, the corresponding quadrant may be left blank.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for acquiring an image, the method including:
using a user interface to select a protocol comprising a protocol list including images to be acquired; and
using a front-end to acquire an image set based at least in part on said protocol and at least one mode, wherein said at least one mode includes an operating mode configured to be toggled between an Autojump On mode and an Autojump Off mode, the Autojump On mode configured to scan a first image in the protocol list and then jump to a next image in the protocol list, the Autojump Off mode configured to scan the first image in the protocol list and not jump to the next image in the protocol list.

2. The method of claim 1, wherein said at least one mode is automatically selected based at least in part on said protocol.

3. The method of claim 1, further including communicating with a measurements package.

4. The method of claim 1, wherein said at least one mode includes an imaging mode.

5. The method of claim 4, wherein said imaging mode includes at least one of B-mode imaging, M-mode imaging, color M-mode imaging, harmonic imaging, tissue velocity imaging, and strain rate imaging.

6. The method of claim 1, wherein said protocol includes a plurality of views.

7. The method of claim 6, wherein said image set includes a plurality of images, and wherein said plurality of images are associated with said plurality of views.

8. The method of claim 6, wherein said plurality of views is represented by a plurality of icons.

9. The method of claim 6, wherein said plurality of views is associated with a plurality of reference images.

10. The method of claim 1, further including at least one of detecting an amplitude of data corresponding to said image set, compressing data corresponding to said image set, filtering clutter associated with said image set, and estimating movement parameters of data corresponding to said image set.

11. The method of claim 1, further including storing said image set.

12. The method of claim 1, wherein said method is a method for acquiring an ultrasound image set of a moving cardiac structure based at least in part on a protocol and at least one mode.

13. A system for acquiring an image, the system including:
a user interface, wherein said user interface is adapted to select a protocol comprising a protocol list including images to be acquired; and
a front-end, wherein said front-end is adapted to acquire an image set based at least in part on said protocol and at least one mode, wherein said at least one mode includes an operating mode configured to be toggled between an Autojump On mode and an Autojump Off mode, the Autojump On mode configured to scan a first image in the protocol list and then jump to a next image in the protocol list, the Autojump Off mode configured to scan the first image in the protocol list and not jump to the next image in the protocol list.

14. The system of claim 13, further including a processor, wherein said processor is adapted to automatically select said at least one mode based at least in part on said protocol.

15. The system of claim 13, further including a processor, wherein said processor is adapted to communicate with a measurements package.

16. A non-transitory computer readable storage medium including a set of instructions for execution on a computer, the set of instructions including:
a selection routine configured to select a protocol based on an input from a user interface, the protocol comprising a protocol list including images to be acquired; and
an acquisition routine configured to use a front-end to acquire an image set based at least in part on said protocol and at least one mode, wherein said at least one mode includes an operating mode configured to be toggled between an Autojump On mode and an Autojump Off mode, the Autojump On mode configured to scan a first image in the protocol list and then jump to a next image in the protocol list, the Autojump Off mode configured to scan the first image in the protocol list and not jump to the next image in the protocol list.

17. The computer readable storage medium of claim 16, wherein said selection routine is configured to automatically select said at least one mode based at least in part on said protocol.

18. The computer readable storage medium of claim 16, wherein said set of instructions further includes a communication routine, wherein said communication routine is configured to communicate with a measurements package.

* * * * *